United States Patent [19]

Williamson et al.

[11] Patent Number: 5,116,506
[45] Date of Patent: May 26, 1992

[54] SUPPORT AERATED BIOFILM REACTOR

[75] Inventors: Kenneth J. Williamson; Sandra Woods, both of Corvallis, Oreg.; Stuart E. Strand, Seattle, Wash.

[73] Assignee: Oregon State University, Corvallis, Oreg.

[21] Appl. No.: 655,206

[22] Filed: Feb. 11, 1991

Related U.S. Application Data

[63] Continuation of Ser. No. 375,269, Jun. 30, 1989, abandoned.

[51] Int. Cl.⁵ ............................................. C02F 3/30
[52] U.S. Cl. ..................................... 210/610; 210/615; 210/630; 210/150; 210/909
[58] Field of Search ............... 210/615, 610, 611, 605, 210/620, 629, 630, 150, 151, 908, 909

[56] References Cited

U.S. PATENT DOCUMENTS

| 4,181,604 | 1/1980 | Onishi et al. | 210/615 |
| 4,416,993 | 11/1983 | McKeown | 210/615 X |
| 4,746,435 | 5/1988 | Onishi et al. | 210/615 |
| 5,057,221 | 10/1991 | Bryant et al. | 210/610 |

Primary Examiner—Thomas Wyse
Attorney, Agent, or Firm—Klarquist, Sparkman, Campbell, Leigh & Whinston

[57] ABSTRACT

A gas permeable membrane divides a reactor vessel into a liquid compartment and a gas compartment. A biofilm is grown on the gas permeable membrane on the liquid side of the membrane. Teh gas permeable membrane is supported by the structure of the membrane itself. The biofilm is chosen from bacteria to degrade cetain pollutants by means of anaerobic fermentation, aerobic heterotrophic oxidation, dehalogenation, and hydrocarbon oxidation. This is accomplished by means of oxygen and alternate gases (i.e., methane) through the gas permeable membrane to certain bacteria growing on the liquid side of the gas permeable membrane.

17 Claims, 1 Drawing Sheet

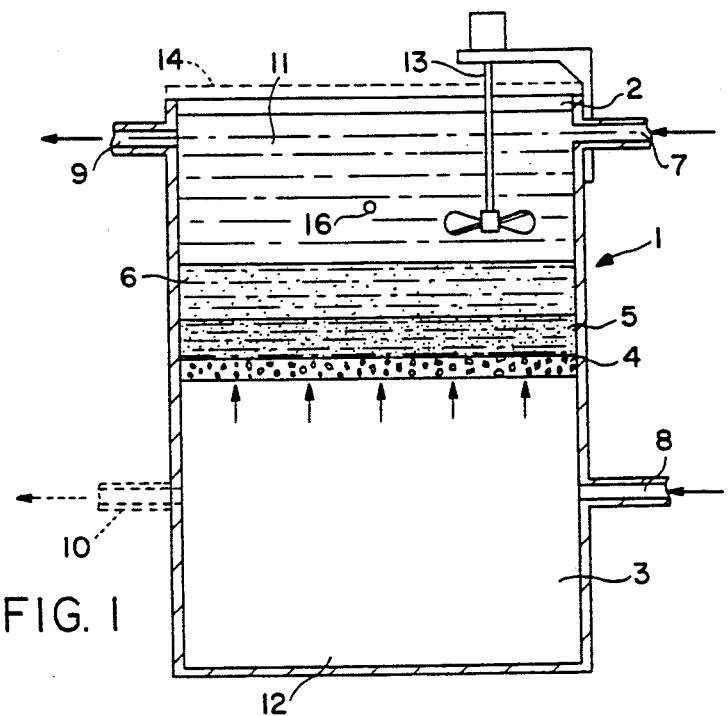
FIG. 1
FIG. 2
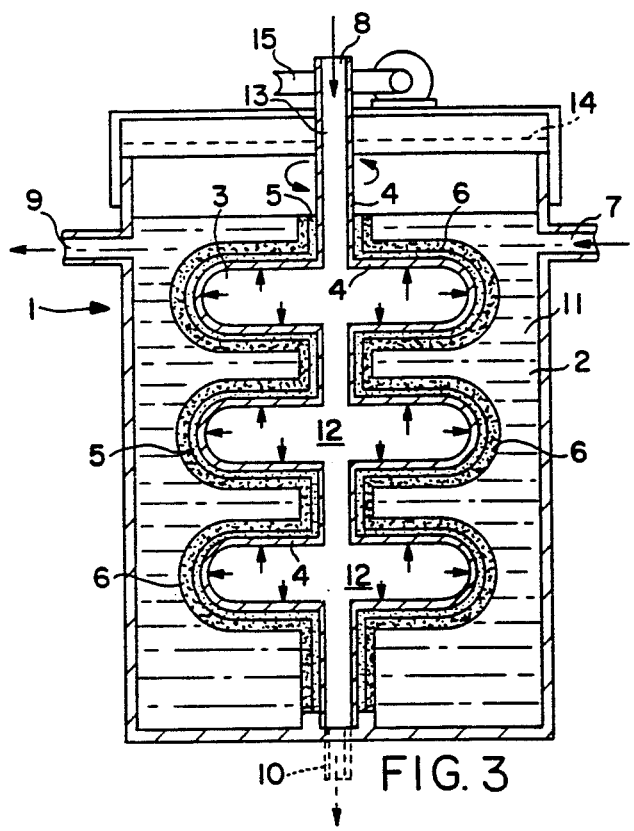
FIG. 3

SUPPORT AERATED BIOFILM REACTOR

The invention disclosed herein was developed in part under NSF grant number CES-8513558-01. The government may have certain rights in this invention.

This application is a continuation of application Ser. No. 07/375,269, filed on Jun. 30, 1989, now abandoned.

BACKGROUND OF THE INVENTION

1. Field of the Invention.

This invention is in the general field of degradative technology by the use of biofilms and, more particularly, in the area of biological treatment reactors containing biofilms supported on a gas permeable membrane.

2. Description of the Prior Art.

In the field of degradative technology, new applications of biofilms are continuing to be developed for selected and non-selective removal of pollutants from both wastewaters and ground waters. Depending upon the depths of the biofilms and relative concentrations of the various potential substrates in the bulk solution, concentrations of the electron donors and electron acceptors in the biofilm can vary over wide ranges, providing several distinct micro-environments or "layers" for growth of various groups of bacteria based upon the electron donor and electron acceptor pairs. These types may include, but are not limited to, aerobic heterotrophic respiration, anaerobic fermentation, nitrification and denitrification.

For the selection of a successful process to treat municipal and various industrial wastes, engineers typically have attempted to control the reactor concentrations of the electron donor or the electron acceptor, and the solids retention time. With the proper control, a process can include various combinations of aerobic heterotrophic oxidation, anaerobic fermentation. In engineering practice, the practice of combining several bacterial groups in a single reactor has resulted in several treatment systems using conventional suspended growth and biofilm reactors. This approach for complex waste often results in a series of separate reactors with associated piping, pumping and clarifiers. However, considerable savings of construction, operation, and maintenance costs may be possible by developing systems that include all bacteria capable of anaerobic fermentation, aerobic heterotrophic oxidation, nitrification and denitrification within a single reactor.

Applicants have previously designed a similar device using oxygen for the removal of nitrogen compounds. The present invention is directed toward a system using oxygen and additional gases.

SUMMARY OF THE INVENTION

In this invention, a gas permeable membrane is supported in a reactor where gaseous substrates are provided by diffusion through a permeable support surface. The reactor solution can be maintained in either an anoxic or oxygenated state and can be mixed either mechanically or by diffused gases. The reactor could operate in a variety of hydraulic regimes including plugflow to completely mix. However, it appears advantageous that a plug-flow mode would be used so that continuous gradients of organics with respect to the reactor length would occur. The reactor can also act as a clarifier to remove the sloughed biomass if mixing were limited. Periodic or continuous mixing would be used to shear organisms so as to maintain desired biofilm depth and high active cell mass.

It is an object of this invention to supply methane or another volitale hydrocarbon at a sufficiently high rate through gas permeable membranes so as to permit the growth of methane or hydrocarbon gases utilizing bacteria in a separate layer of the biofilm.

It is another further object to isolate the anaerobic layer near the organics in the liquid compartment to enhance mass transfer which is especially important for high strength waste.

Another object is to enclose the oxygen supply to increase efficiency of transfer, to allow the reactor to be opened to the atmosphere, and to avoid aeration of liquid compartment.

Another further object is to allow the mixing to be controlled independent of aeration so as to facilitate deep biofilms, long solid retention times, limited sloughing, and solids removal within the biological treatment reactor.

It is a further object to lower construction costs due to fewer reactors and associated piping and pumping.

It is another further object to decrease operation costs due to the elimination of recycled streams and increased oxygen transfer efficiencies.

It is an object to increase flexibility and operation due to a great adaptability to a wide range of waste with wide ratios of carbon and nitrogen and to a wide variety of wastes.

It is a further object to provide high stability due to the long solid retention times in the deep biofilms.

It is another further object to facilitate the biological removal of halogenated compounds that require the presence of both aerobic and anaerobic pathways for complete dehalogenation and oxidation.

It is a further object to facilitate the biological removal of low-molecular weight halogenated compounds by hydrocarbon degraders by providing both oxygen and another gas such as methane, propane, or other hydrocarbon to diffuse through the gas permeable membrane.

It is a final object to provide removal within a single reactor degrading refactory compounds such as chlorinated phenols and chlorinated biphenyls, halogenated phenols, halomethanes, haloethanes that require alternate degradation with an aerobic and anaerobic environments.

DESCRIPTION OF THE DRAWINGS

FIG. 1 is a view showing a schematic view of the reactor.

FIG. 2 is a view showing a reactor tank with a liquid flowing through pillow layers of the biofilm mass.

FIG. 3 shows a gas permeable membrane and biofilm that rotates within a bulk liquid reactor tank.

DESCRIPTION OF THE PREFERRED EMBODIMENT

The following example describes the combined aerobic heterotrophic oxidation, anaerobic fermentation, and the degradation of chloromethanes by methylotrophs in a gas permeable membrane supported biofilm.

Methylotrophs are aerobic bacteria that are capable of growth using reduced single carbon compounds, such as methane and methanol, as a carbon source. Most are mesophilic. They can use a number of single carbon compounds to support growth, the sole requirement seeming to be that no carton-carbon bonds be present.

Many are pigmented, with colors ranging from pink to yellow to ivory, and most form a resting stage during times of unfavorable growth conditions. Methane oxidation to methanol is catalyzed by the methane monooxygenase (MMO) enzyme. Methanol is further oxidized to formaldehyde, formate, and eventually to water and carbon dioxide using other constituative enzymes.

Methylotrophs are ubiquitous and quite versatile. About half of the total organic carbon degraded anaerobically in nature is converted to methane, yet the amount of hydrocarbon reaching the atmosphere amounts to only about 0.5 percent of the total carbon turnover. Oxidation of methane by methylotrophs reportedly accounts for much of the difference between the total methane produced and that reaching the atmosphere. Methylotrophs have been isolated that are capable of growth on glucose and other substrates in addition to methane and/or methanol, and thermophilic methylotrophs have also been isolated. The ability to fix hydrogen has been demonstrated for some methylotrophs as well as the ability to perform dehalogenation. Further, there is also reported a methylotroph capable of growth using methylene chloride as its sole carbon source.

A great deal of work has been done to better understand the biochemistry of the methylotrophs, especially regarding the MMO enzyme and its ability to act as a biological catalyst to oxidyze compounds that cannot support methylotrophic growth. Furthermore, additional research has suggested involvement of the MMO enzyme in dehalogenating haloalkanes and was found to be effective in degrading chlorinated ethenes. Previous research has indicated that at least 44 compounds including n-alkanes, n-alkenes, ethers, and aromatic, alicyclic and heterocyclic compounds have been shown to be vulnerable to co-oxidation by methylotrophs.

The MMO enzyme may be present in either a soluble or a particulate state, however, the soluble form of the enzyme is more effective in oxidizing various organic compounds than the particulate form. The tendency for the enzyme to be present in one form or the other has been shown to depend on the copper ion concentration in the media and the amount of biomass present, with a low copper ion concentration in a high biomass favoring the soluble form of the enzyme. In addition to being effective at oxidizing a more diverse range of compounds, soluable MMO has been shown to be less susceptible to inhibition than the particulate form. Also, mixed cultures of methylotrophs have been shown to be less susceptible to inhibition than pure cultures.

Several researchers have speculated that the broad specificity of the MMO enzyme could make methylotrophs suitable for use as biocatalysts in commercial biotransformation applications or in waste/wastewater treatment systems to treat recalcitrant compounds by co-oxidative means. Efforts are underway to create conditions in the ground water favorable to in situ degradation of chlorinated organic compounds by methylotrophs. This type of approach would be advantageous in that the contaminated ground water would not need to be pumped to the surface for treatment. Also, this approach would rely primarily on a biofilm type of growth. Biofilms tend to be very stable and effective in treating low-level concentrations of organics.

The use of a gas-permeable membrane to support the biofilm allows the selection and control of conditions which are conducive to multi-layer growth of specific organisms of interests and enhances their long term retention within the system. Using a gas permeable membrane supported biofilm approach, it is possible to provide a combination of aqueous and gaseous substrates to the two sides of the biofilm. In this manner multiple layers of bacterial cultures may be grown, transitioning from strict aerobes nearest the gas compartment (where oxygen is supplied), through a layer of microaerophiles and ultimately to a layer of anaerobes adjacent to the bulk liquid.

In the design of the apparatus, a reactor is constructed of a top portion and a bottom portion. The reactor in the top portion or liquid compartment contains ports for adding and removing nutrient solution. The lower portion or gas compartment contains influent and effluent ports for adding and removing gases. The top portion and lower portion are joined together such that a gas permeable membrane may be joined at the point where the top portion and lower portion of the reactor join together. The bio-support gas permeable membrane that was selected for use was a teflon/nylon laminate, commonly known as Gore-tex (TM) of Gore and Associates. In the top portion of the reactor a mixing rod or plurality of mixing rods may be placed with means for rotation. Air or oxygen is chosen and is supplied to the gas compartment where, by diffusion, it will pass through the selected membrane, in this case Gore-tex(TM), and be available to the biofilm which is seeded on the liquid side of the gas permeable membrane.

In the design of the apparatus, a reactor is constructed of top portion and a bottom portion. The reactor in the top portion or liquid compartment contains ports for adding and removing nutrient solution. The lower portion or gas compartment contains influent and effluent ports for adding and removing gases. The top portion and lower portion are joined together such that a gas permeable membrane may be joined at the point where the top portion and lower portion of the reactor join together. The bio-support gas permeable membrane that was selected for use was a microporous teflon/nylon laminate, commonly known as gortex (TM). In the top portion of the reactor a mixing rod or plurality of mixing rods may be placed with means for rotation. An appropriate gas is chosen and is supplied to the gas compartment where, by diffusion, it will pass through the selected membrane, in this case gortex (TM), and be available to the biofilm which is seeded on the liquid side of the gas permeable membrane.

In order to beqin the biofilm, a bacterial seed consisting of thickened effluent from a municipal wastewater treatment plant and thickened sludge from an anaerobic reactor was used. The culture was enriched for methylotrophs by providing methane as a principal carbon source and maintaining a moderate flow of nutrient solution to wash out undesired organisms.

With regard to the operations of this particular system, methane and oxygen are provided to the gas chamber in a ratio of 50 percent methane and 50 percent oxygen. The stoichiometry for methane oxidation by methylotrophs is: $1 CH_4 + 1.0$ to $1.1\ O_2 \rightarrow 0.2$ to $0.3\ CO_2$. It is expected that methane oxidation rates of between 19.2 and 30 mmol of methane per day per gram of biomass where the biomass is the total bacterial mass divided by the area of the gas permeable membrane.

The degradation of chlorinated methanes by the gas permeable membrane support biofilm allows the MMO enzyme to oxidize monochloromethane, methylene chloride and chloroform. Up to two chlorine substitutions did not impede the ability of the enzyme to oxidize the compounds, but more than two substitutions slowed the rate of oxidation, in that the enzyme was not able to oxidize fully substituted methanes. This follows the observed research results.

For dehalogenation of substituted n-alkanes by oxygenase enzymes the dechlorination of a terminal chlorine atom occurs according to the following reaction sequence: R—$CH_2CL$ oxygenase R—CHCLOH spontaneous R—CHO dehydrogenase R—COOH. Furthermore, sequential degradation of substrates appears to occur such that methylene chloride degrades at a faster rate than chloroform.

A reactor combining aerobic hetertrophic oxidation and anaerobic fermentation activity in a single biofilm was achieved by supplying the gas chamber of the reactor with oxygen and methane. The treated liquid was filtered sewage and the bulk solution in the reactor was anoxic. Within deep biofilms concentrations of electron donors and electron acceptors may vary over wide ranges, providing several distinct micro-environments or "layers". These micro-environments select for the growth of bacteria based upon the electron donor/acceptor pairs associated with aerobic heterotrophic oxidation or anaerobic fermentation. This optimizes the population for three organism types (aerobic heterotrophic respiration, anaerobic fermentation, and the liquid compartment containing filtered primary effluent).

The biofilm continued to grow, which was consistent with the assumption of aerobic conditions in the biofilm near the support.

This method can be used in several configurations. The reactor solution can be maintained in either an anoxic or oxygenated state and can be mixed mechanically or by diffuse gases (excluding nitrogen). The reactor could be designed to operate in a plug flow mode so the continuous gradients of organics were established with respect to reactor length. If mixing were limited the reactor could also act as a clarifier to remove the slough biomass. Periodic high mixing would be used to hear organisms to maintain a desired biofilm depth and high active cell mass.

With the outer solution maintained in an anoxic state, a deep biofilm on the permeable membrane hypothetically would have three zones of microbial activity: an anaerobic fermentation layer near the liquid surface, and heterotrophic oxidation.

With this example we have seen the general outlines of the method and apparatus used. The apparatus comprises a reactive vessel divided into a liquid compartment and a gas compartment by means of a gas permeable membrane where a biofilm of selected microbes grows on the liquid side of the gas permeable membrane. The gas permeable membrane transfers oxygen and methane at a sufficiently high rate to sustain the growth of a biofilm useful in the treatment of wastewaters containing high levels of carbonaceous wastes.

The method used involves the steps of

1. Placing a gas permeable membrane in an enclosed reactor so that two compartments are formed, one a liquid compartment and the other a gas compartment;

2. Seeding the liquid side of the gas permeable membrane by means of the liquid in the liquid compartment;

3. Providing oxygen and methane to the gas compartment; and

4. Providing a flow of liquids through the liquid compartment.

Additionally one or any combination of the following steps can be used:

5. Stirring the liquid in the liquid compartment;

6. Moving the gas permeable membrane through the liquid in the liquid compartment;

7. Diffusing a gas through the liquid in the liquid compartment; or

8. Moving the liquid through the liquid compartment where the gas permeable membrane is fixed in position.

Step 1 can be modified so that the liquid compartment is open to the atmosphere and the gas compartment remains enclosed. In the preferred embodiment, Step 4 is modified so that at the flow is a plug flow.

Step 2 may be preceded by exposing the liquid to the alternate gases to encourage growth of organisms which can survive and/or thrive in the alternate gases.

With respect to the apparatus used, FIG. 1 shows a reactor 1 with a liquid compartment 2 and a gas compartment 3. A gas permeable membrane 4 divides the reactor 1 into the liquid compartment 2 and the gas compartment 3. On the liquid side of the gas permeable membrane 4 an aerobic layer of biofilm 5 and an anaerobic layer of biofilm 6 forms. The liquid ingress 7 provides the bulk liquid 11 which is removed from the liquid compartment 2 by means of the liquid egress 9. Similarly, the gas compartment 3 contains a gas ingress 8 with an optional gas egress 10. The bulk liquid 11 in the liquid compartment 2 may, for example, be wastewater. The gas compartment 3 is filled with oxygen 12. A mechanical mixer 13 provides the means for mixing the liquid in the liquid compartment. A diffuser 16 may also be used in the liquid compartment to diffuse gases through the liquid 11 in order to mix the liquids. A reactor top 14 may be provided or may not be provided depending upon the method used.

FIG. 2 shows the reactor 1 where pillows 17 are used. The pillows 17 are made up of the gas permeable membrane 4. In this reactor 1, the liquid 11 flows around the pillows 17 which are supplied with oxygen 12 from the bottom of the reactor 1.

FIG. 3 shows a reactor 1 with a gas compartment 3 formed by the gas permeable membrane 4 in such a fashion that the gas permeable membrane 4 may be rotated through the liquid 11 in the liquid compartment 2. The biofilms 5 and 6 will form on the gas permeable membrane 4 as previously discussed.

While different methods and apparatuses have been disclosed in the illustrative material herein, other modifications within the scope of the invention will occur to those skills in this particular art. Specifically, gases other than methane may be used. It is therefore desired that the invention be measured by the appended claims rather than by the purely illustrative material of the specification.

We claim:

1. A method of treating liquid waste, comprising the steps of:

providing a reactor having a gas permeable membrane that divides the reactor into a liquid compartment for the liquid waste and a gas compartment for a gas;

providing a biofilm layer on the liquid compartment side of the membrane, the layer comprising a first layer of aerobic organisms adjacent the membrane, and a second layer of anaerobic organisms between the aerobic layer and liquid;

introducing an oxygen containing gas into the gas compartment, and allowing it to diffuse through the membrane; and introducing a liquid waste into the liquid compartment and allowing it to react with the biofilm layer.

2. The method of claim 1 wherein the step of introducing a liquid waste comprises introducing a nitrogen containing waste into the liquid compartment.

3. The method of claim 1 wherein the step of providing a biofilm layer comprises introducing a gas into the gas compartment that diffuses through the membrane and selects gas degrading organisms in the biofilm layer.

4. The method of claim 3 wherein the step of providing a biofilm layer comprises introducing a gas into the gas compartment which selects methylotrophs in the biofilm layer.

5. The method of claim 4 wherein the step of introducing the gas comprises introducing a gas comprising methane in sufficient amounts to promote growth of methylotrophic bacteria in the biofilm layer.

6. The method of claim 5 wherein the step of introducing the gas comprises introducing a gas comprising about 50% methane by volume to diffuse through the membrane and promote growth of methylotrophic bacteria in the anaerobic layer.

7. The method of claim 1 wherein the step of providing the biofilm layer comprises seeding the liquid side of the gas permeable membrane by introducing the liquid waste into the liquid compartment.

8. The method of claim 7 wherein the step of providing the biofilm layer further comprises seeding the biofilm from waste containing aerobic and anaerobic bacteria.

9. The method of claim 1 further comprising the step of providing relative movement between the liquid and biofilm layer.

10. The method of claim 9 wherein the step of providing relative movement comprises moving the membrane through the liquid in the liquid compartment.

11. The method of claim 9 wherein the step of providing relative movement comprises stirring the liquid in the liquid compartment.

12. The method of claim 1 further comprising the step of enclosing the liquid layer in a container to exclude sources of oxygen other than oxygen through the membrane.

13. The method of claim 1 further comprising the step of maintaining the liquid in substantially anaerobic condition.

14. The method of claim 1 further comprising the step of introducing a gas into the liquid layer through other than the membrane.

15. The method of claim 1 wherein the step of introducing a liquid waste comprises introducing a waste that requires biodegradation sequentially between an anaerobic and an aerobic layer.

16. The method of claim 1 wherein the step of introducing the liquid waste further comprises introducing waste selected from the group consisting of chlorinated phenols, chlorinated biphenyls, halogenated phenols, halomethanes, and haloethanes.

17. A reactor for treating liquid waste, comprising a reactor having a gas permeable membrane that divides the reactor into a liquid compartment for the liquid waste and a gas compartment for a gas;

a biofilm layer on the liquid compartment side of the membrane, the layer comprising a first layer of aerobic organisms adjacent the membrane, and a second layer of anaerobic organisms between the aerobic layer and liquid;

a means for introducing an oxygen containing gas into the gas compartment, and means for allowing the gas to diffuse through the membrane without mixing the first and second layers; and means for introducing a liquid waste into the liquid compartment and allowing it to react with the biofilm layer.

* * * * *